US005685292A

United States Patent [19]
Fenn

[11] Patent Number: 5,685,292
[45] Date of Patent: Nov. 11, 1997

[54] NASAL TIP-LIFT ADHESIVE BAND FOR IMPROVED BREATHING

[76] Inventor: Arthur C. Fenn, 5 Parkside Way, Greenbrae, Calif. 94904

[21] Appl. No.: 675,356

[22] Filed: Jul. 5, 1996

[51] Int. Cl.⁶ .................. A61M 15/00; A61M 16/10; A61F 5/08; A62B 7/00
[52] U.S. Cl. .................. 128/200.24; 128/207.18; 606/199; 606/204.45
[58] Field of Search .................. 128/200.24, 207.18, 128/898; 602/902, 54, 58; 606/199

[56] References Cited

U.S. PATENT DOCUMENTS

| | | | |
|---|---|---|---|
| 5,476,091 | 12/1995 | Johnson | 128/200.24 |
| 5,533,503 | 7/1996 | Doubek | 128/200.24 |
| 5,546,929 | 8/1996 | Muchin | 128/200.24 |

Primary Examiner—J. Miller
Assistant Examiner—Richard N. Wieland
Attorney, Agent, or Firm—Thomas W. Tolpin

[57] ABSTRACT

An adhesive band is designed for use on the nose to improve breathing through the nose. The bottom part is triangular shaped to fit the tip of the nose. The middle part is made narrow to fit over the bridge of the nose. The top part is rectangular to fit on the forehead. The application of this band to the nose in an upward pulling manner lifts the tip of the nose. This new more horizontal position of the nasal tip allows for easier nasal breathing by reducing resistance of air entering the nose. The principles of this invention have been described in this application. Variations and changes may be made by those skilled in this art without departing from the spirit of the invention.

6 Claims, 1 Drawing Sheet

NASAL TIP-LIFT ADHESIVE BAND FOR IMPROVED BREATHING

BACKGROUND OF THE INVENTION

1. Field of the Invention

This invention pertains to an adhesive band which improves the nasal airway by lifting the nasal tip.

2. Description of the Prior Art

There is available an adhesive strip which improves breathing through the nose by pulling on the sides of the nose widening the nasal passages. These stripes do not provide the novel improvement of the invention herein disclosed. This invention improves nasal breathing by a different method which comprises lifting the nasal tip.

SUMMARY

A primary object of the present invention is to provide a method to improve nasal breathing. This invention provides an adhesive band which is so designed that by applying one end of the band to the nasal tip and the other end to the forehead, the resulting upward lift of the nasal tip improves breathing.

This adhesive band is triangular shaped on one end, narrow in the middle, and rectangular shaped on the other end.

The triangular end is applied to the nasal tip. While pulling upward, the middle narrow portion is applied to the nasal bridge, and the rectangular portion is applied to the forehead. The result is that the nasal tip is lifted upward improving breathing through the nose.

DESCRIPTION OF THE PREFERRED EMBODIMENTS

Figure 1:
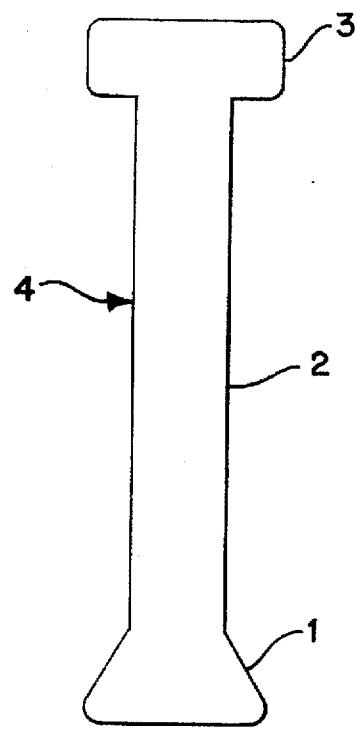
FIG. 1 is a perspective view of the adhesive band.
Figure 2:
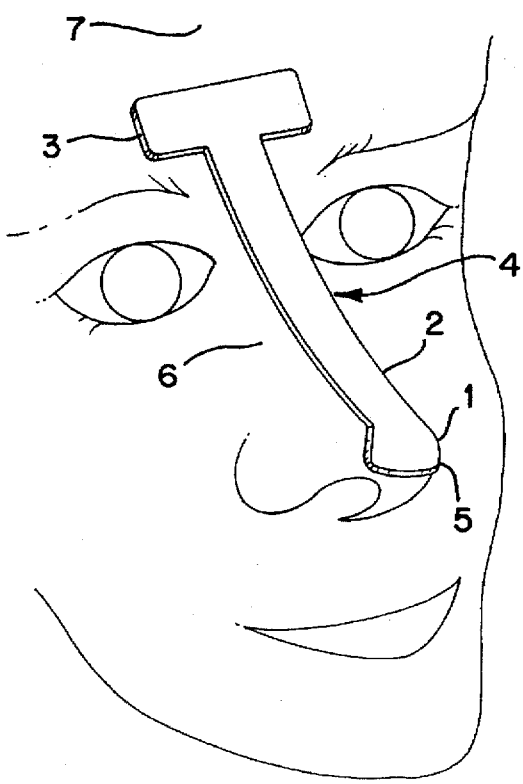
FIG. 2 is an oblique drawing of a nose illustrating the adhesive band on the nose.

The FIG. 1 drawing illustrates an adhesive band generally designated 4. The adhesive band 4 has a triangular end 1 and a rectangular end 3. 1 and 3 are connected by a middle narrow portion 2. The FIG. 2 drawing illustrates the adhesive band 4 adhering to the nose 6 and forehead 7. The band 4 extends from the tip of the nose 5, on to the bridge of the nose 6, and ends on the forehead 7. The bottom triangular portion 1 is placed on the tip of the nose 5.

The narrow portion 2 is placed on the nasal bridge 6, and the rectangular portion 3 is placed on the forehead 7.

The bottom triangular portion 1 is applied to the tip of the nose 5. While pulling upward on the band 4, the narrow portion 2 is applied to the bridge of the nose 6. Finally while continuing to pull upward, the rectangular portion 3 is applied to the forehead 7. The result is that the tip of the nose 5 is lifted upward and held in position by the adhesive band 4. When the tip of the nose 5 is lifted upward, resistance to air entering the nose is reduced thus improving nasal breathing.

I claim:

1. A method to improve breathing through a wearer's nose using an elongated adhesive band having a triangular end, a rectangular end and a narrow middle part therebetween, comprising the steps of:

applying the triangular end of the adhesive band to the tip of the wearer's nose, applying the middle part of the adhesive band to the bridge of the wearer's nose while pulling upward on the adhesive band, and applying the rectangular end of the adhesive band to the wearer's forehead while continuing the upward pulling.

2. A method to improve breathing through a wearer's nose using an elongated adhesive band having a first end, a second end and a middle part therebetween, comprising the steps of:

applying the first end of the adhesive band to the tip of the wearer's nose, applying the middle part of the adhesive band to the bridge of the wearer's nose while pulling upward on the adhesive band, and applying the second end of the adhesive band to the wearer's forehead while continuing the upward pulling.

3. A method as defined in claim 2 wherein the step of applying the first end comprises applying a triangular shaped end of the adhesive band to the tip of the wearer's nose.

4. A method as defined in claim 2 wherein the step of applying the first end comprises applying a triangular shaped end of the adhesive band, the triangular shape being substantially twice the width of the narrow middle part.

5. A method as defined in claim 2 wherein the step of applying the second end comprises applying a rectangular shaped end of the adhesive band to the wearer's forehead while continuing the upward pulling.

6. A method as defined in claim 2 wherein the step of applying the second end comprises applying a rectangular shaped end of the adhesive band, the rectangular shape being substantially twice the width of the narrow middle part.

* * * * *